(12) United States Patent
Cheon et al.

(10) Patent No.: US 10,487,052 B2
(45) Date of Patent: Nov. 26, 2019

(54) SYNTHESIS METHOD OF N-SUBSTITUTED MALEIMIDE USING SOLID ACID CATALYSTS

(71) Applicant: LG CHEM, LTD., Seoul (KR)

(72) Inventors: Joo Young Cheon, Daejeon (KR); Jun Seon Choi, Daejeon (KR); Ji Yeon Kim, Daejeon (KR); Wang Rae Joe, Daejeon (KR); Kyung Soo Kim, Daejeon (KR); Eung Seob Yeom, Daejeon (KR); Won Kyun Lee, Daejeon (KR)

(73) Assignee: LG CHEM, LTD., Seoul (KR)

(*) Notice: Subject to any disclaimer, the term of this patent is extended or adjusted under 35 U.S.C. 154(b) by 0 days.

(21) Appl. No.: 16/091,475

(22) PCT Filed: Nov. 6, 2017

(86) PCT No.: PCT/KR2017/012499
§ 371 (c)(1),
(2) Date: Oct. 4, 2018

(87) PCT Pub. No.: WO2018/124453
PCT Pub. Date: Jul. 5, 2018

(65) Prior Publication Data
US 2019/0152910 A1    May 23, 2019

(30) Foreign Application Priority Data

Dec. 28, 2016   (KR) .................. 10-2016-0181021
Oct. 13, 2017   (KR) .................. 10-2017-0133529

(51) Int. Cl.
| | |
|---|---|
| C07D 207/452 | (2006.01) |
| B01J 27/16 | (2006.01) |
| B01J 27/28 | (2006.01) |
| B01J 31/12 | (2006.01) |
| C07D 207/448 | (2006.01) |
| B01J 38/50 | (2006.01) |

(52) U.S. Cl.
CPC .......... *C07D 207/452* (2013.01); *B01J 27/16* (2013.01); *B01J 27/285* (2013.01); *B01J 31/12* (2013.01); *C07D 207/448* (2013.01); *B01J 38/50* (2013.01); *Y02P 20/584* (2015.11)

(58) Field of Classification Search
None
See application file for complete search history.

(56) References Cited

U.S. PATENT DOCUMENTS

| | | |
|---|---|---|
| 4,786,738 A | 11/1988 | Kita et al. |
| 2011/0124882 A1 | 5/2011 | Kim et al. |

FOREIGN PATENT DOCUMENTS

| | | |
|---|---|---|
| CN | 101670294 B | 8/2014 |
| EP | 0213933 A2 | 3/1987 |
| KR | 10-0087131 B1 | 3/1995 |
| KR | 10-2009-0069016 A | 6/2009 |
| KR | 10-1051543 B1 | 7/2011 |
| WO | 2010018926 A2 | 2/2010 |
| WO | 2018038415 A1 | 3/2018 |

OTHER PUBLICATIONS

International Search Report for PCT/KR2017/012499 filed on Nov. 6, 2017.
Junpingzhuang et al., "Selective Catalytic Conversion of Glucose to 5-hydroxymethylfurfural over Zr(H2PO4)2 Solid Acid Catalysts", Advanced Materials Research, 2011, p. 134-137, Vols. 236-238, Trans Tech Publications, Switzerland.
Yuichi Kamiya et al., "Zirconium phosphate with a high surface area as a water-tolerant solid acid", Catalysis Letters, Apr. 2004, p. 45-47, vol. 94, Nos. 1-2, Plenum Publishing Corporation.
European Search Report issued in related application No. EP 17887093.7 on Feb. 14, 2019.

*Primary Examiner* — Po-Chih Chen

(57) ABSTRACT

The present invention relates to a synthesis method of N-substituted maleimides using a non-homogeneous solid acid catalyst, and particularly, a synthesis method of N-substituted maleimides with high synthesis yield by using a zirconium(IV) hydrogen phosphate as a catalyst, by which, the loss of the catalyst is minimized, the separation and recovering processes of the catalyst are simplified, in case when the activity of the separated and recovered catalyst is decreased, the complete regeneration of the catalyst is possible via washing or firing, and solvents that could be used during a washing process of the catalyst are not limited.

11 Claims, 2 Drawing Sheets

SYNTHESIS METHOD OF N-SUBSTITUTED MALEIMIDE USING SOLID ACID CATALYSTS

CROSS-REFERENCE TO RELATED APPLICATIONS

This application is a U.S. National Stage of PCT/KR2017/012499, filed Nov. 6, 2017, which claims the benefit of Korean Patent Application Nos. 10-2016-0181021, filed on Dec. 28, 2016, and 10-2017-0133529, filed on Oct. 13, 2017 in the Korean Intellectual Property Office, the disclosures of which are incorporated herein in their entirety by reference.

TECHNICAL FIELD

The present invention relates to a synthesis method of an N-substituted maleimide using a zirconium(IV) hydrogen phosphate as a solid acid catalyst.

BACKGROUND ART

Maleimide compounds are compounds useful as resin raw materials, raw materials for medicines and agricultural chemicals, and particularly, used as one of copolymerization components for improving the heat resistance of styrene-based resins such as ABS resins, AS resins, AB resins, ACS resins, AES resins and AAS resins, polyvinyl chloride resins, polymethyl methacrylate resins, phenol resins, or the like. Among them, N-phenyl maleimides (hereinafter, will be also referred to as PMI) are excellent regarding reactivity or heat resistance and are particularly widely used.

As the methods for preparing maleimide compounds, various methods are known since before, such as 1) a producing method via dehydration reaction of maleic anhydride (hereinafter, will be also referred to as MAH) and primary amines in one-step, 2) a producing method by producing maleamic acids from maleic anhydrides and primary amines and performing the dehydration ring-closure imidization reaction of the maleamic acids, and 3) a producing method via the ring-closure imidization reaction of corresponding maleamic acid monoesters.

Among the methods, in the 1) producing method from maleic anhydride and primary amines in one-step, defects of low productivity due to still low yields arise, and in the 3) producing method from maleamic acid monoesters, defects of remaining and inclusion of alcohols produced by the ring-closure imidization reaction in products arise. Accordingly, industrially, the 2) producing method via the dehydration ring-closure imidization reaction of maleamic acids is generally conducted.

Meanwhile, the primary amine during preparing N-phenyl maleimides is aniline (hereinafter, will be also referred to as ANL), and the maleamic acid is N-phenyl maleamic acid (hereinafter, will be also referred to as PMA).

Most of the catalysts used in the conventional 2) synthesis method of N-phenyl maleimides directly use a liquid phase catalyst which is a homogeneous system, or a catalyst carrying an active component with a homogeneous system in a carrier. However, in this case, the active component may be lost due to water which is a by-product produced during the synthesizing N-phenyl maleimides, and defects of difficult supplement and regeneration of the lost active component may arise. Also, complicated problems may arise regarding the separation process of catalysts including the limitation of solvents used for separating catalysts, the generation of a large amount of waste water in the removing process of remaining catalysts and impurities, and requirements on energy input due to the execution of cooling and heating.

Therefore, the present inventors studied to solve the above-described defects and found that the above-described defects could be solved by using a zirconium(IV) hydrogen phosphate which is a solid acid catalyst in the synthesis method of N-phenylmaleimides of 2) and completed the present invention.

PRIOR ART DOCUMENT

Patent Document (Patent Document 1) Korean Registration Patent Publication No. 10-1051543 (registered at Jul. 18, 2011)

DISCLOSURE OF THE INVENTION

Technical Problem

An aspect for solving of the present invention is to provide a synthesis method of N-substituted maleimides, not requiring the supplement of a catalyst during synthesis reaction by minimizing the loss of the catalyst by using a zirconium(IV) hydrogen phosphate solid acid catalyst as the catalyst of the synthesis reaction of N-substituted maleimides.

In addition, another aspect for solving of the present invention is to provide a synthesis method of N-substituted maleimides, by which, the separation and recovery of the solid acid catalyst is possible via simple filtering, and the separation and recovering processes thereof are simplified, in case when the activity of the separated and recovered catalyst is decreased, the complete regeneration of the catalyst is possible via washing or firing, and solvents that could be used during a washing process of the catalyst are not limited.

In addition, further another aspect for solving of the present invention is to provide a synthesis method of N-substituted maleimides, by which the synthesis yield of the N-substituted maleimides is high.

Technical Solution

According to an aspect of the present invention, there is provided a synthesis method of N-substituted maleimides, including:

1) a step of injecting maleic anhydride and a primary amine in the presence of an organic solvent and a catalyst to synthesize N-substituted maleimides; and 2) a step of separating the catalyst from a solution including the N-substituted maleimides, wherein the catalyst is a zirconium(IV) hydrogen phosphate solid acid catalyst.

Advantageous Effects

The synthesis method of N-substituted maleimides of the present invention uses a zirconium hydrogen phosphate solid acid catalyst during the synthesis reaction of the N-substituted maleimides and thus, minimizes the loss of a catalyst and does not require the supplement of the catalyst during performing the synthesis reaction.

In addition, the solid acid catalyst may be separated and recovered by simple filtering, and the separating and recovering processes of the catalyst is simple, the complete regeneration of the catalyst via washing or firing is possible, and the washing solvent used during the catalyst washing process may be used without limitation of any type.

In addition, the zirconium hydrogen phosphate solid acid catalyst has effect of a high synthesis yield of N-substituted maleimides.

BRIEF DESCRIPTION OF THE DRAWINGS

The following drawings attached to the specification illustrate preferred examples of the present invention, and serve to enable technical concepts of the present invention to be further understood together with detailed description of the invention given above, and therefore the present invention should not be interpreted only with matters in such drawings.

MODE FOR CARRYING OUT THE INVENTION

Hereinafter, the present invention will be described in more detail to allow for the understanding of the present invention. In this case, it will be understood that words or terms used in the specification and claims shall not be interpreted as the meaning defined in commonly used dictionaries. It will be further understood that the words or terms should be interpreted as having a meaning that is consistent with their meaning in the context of the relevant art and the technical idea of the invention, based on the principle that an inventor may properly define the meaning of the words or terms to best explain the invention.

The present invention provides a synthesis method of N-substituted maleimides, including:

1) a step of injecting maleic anhydride and a primary amine in the presence of an organic solvent and a catalyst to synthesize N-substituted maleimides; and 2) a step of separating the catalyst from a solution including the N-substituted maleimides, wherein the catalyst is a zirconium(IV) hydrogen phosphate solid acid catalyst.

Figure 1:
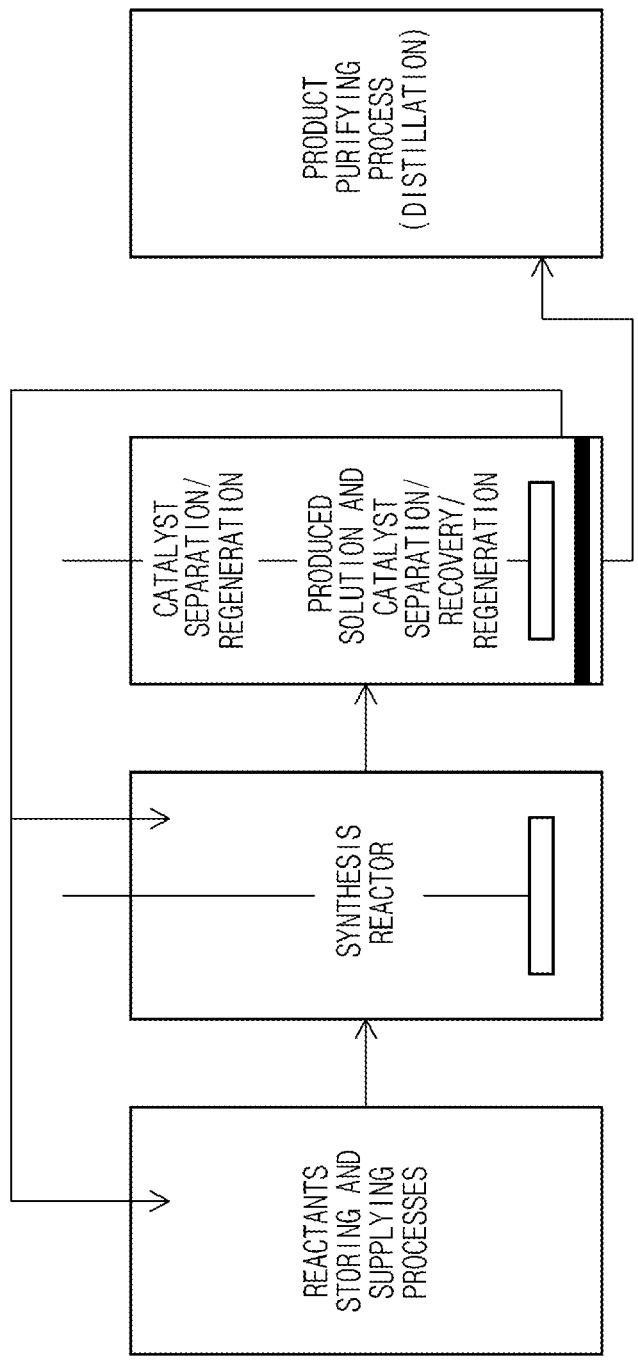
FIG. 1 is a flowchart showing the sequence of the synthesis method of N-substituted maleimides of the present invention.
Figure 2:
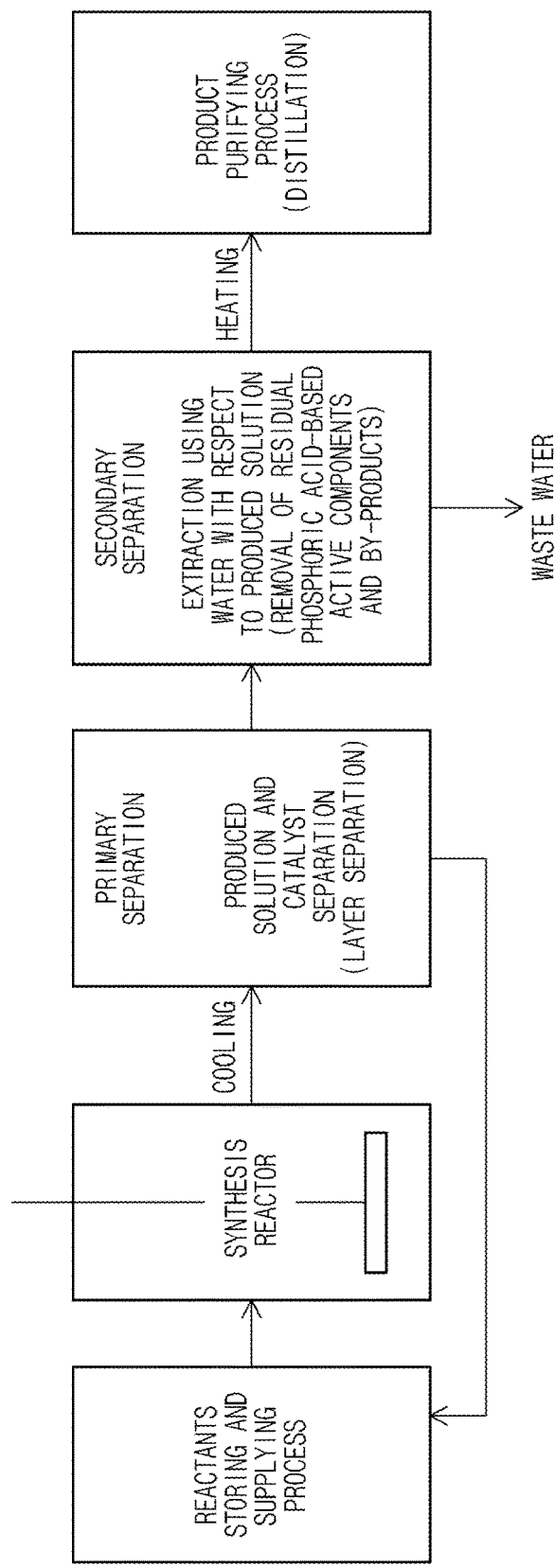
FIG. 2 is a flowchart showing the sequence of the conventional synthesis method of N-substituted maleimides.

Hereinafter, the synthesis method of N-substituted maleimides of the present invention will be explained in detail step by step with reference to FIG. 1.

Step 1)

Step 1) according to an embodiment of the present invention is characterized in synthesizing N-substituted maleimides by injecting maleic anhydride and primary amines in the presence of an organic solvent and a catalyst, as a step for synthesizing N-substituted maleimides.

As the methods for preparing maleimide compounds, various methods are known, including 1) a producing method via dehydration reaction of maleic anhydride and primary amines in one-step, 2) a producing method by producing maleamic acids from maleic anhydride and primary amines and performing the dehydration ring-closure imidization reaction of the maleamic acid, and 3) a producing method via ring-closure imidization reaction of corresponding maleamic acid monoesters.

However, in the 1) producing method from maleic anhydride and primary amines in one-step, defects of low productivity due to still low yields arise, and in the 3) producing method from maleamic acid monoesters, defects of remaining and inclusion of alcohols produced by ring-closure imidization reaction in products arise. Accordingly, the synthesis method of N-substituted maleimides of the present invention will be explained in detail with reference to an embodiment of the 2) producing method via the dehydration ring-closure imidization reaction of maleamic acids.

In the synthesis method of N-substituted maleimides of the present invention, N-substituted maleimides may be synthesized by a method including heating maleic anhydride and a primary amine to perform acylation reaction to produce N-substituted maleamic acids as intermediates in a first step, and performing dehydration ring-closure imidization reaction of the N-substituted maleamic acids at the surface of a catalyst in a second step.

In addition, in the process for obtaining N-phenyl maleamic acid from the maleic anhydride and aniline, maleic anhydride or aniline may be used as they are, but may preferably be used in a solution type dissolved in an organic solvent. Meanwhile, in case of using a solution type obtained by dissolving maleic anhydride or aniline in an organic solvent, subsequent dehydration ring-closure imidization reaction of N-phenyl maleamic acid may be performed as it stands in the solution (organic solvent).

The organic solvent used in the present invention is required to be insoluble in or immiscible with water, be inactive to the reaction and not participate in the reaction so as to emit water produced by the dehydration ring-closure reaction of N-substituted maleic acid out of the system via azeotropic distillation.

In addition, an organic solvent having the boiling point of at least 50° C. or more for the smooth operation of the reaction and the boiling point of less than 170° C. for the stability of produced N-substituted maleimide, is appropriate. Examples of the organic solvents appropriate for the reaction may include benzene, toluene, xylene, o-xylene, ethylbenzene, isopropylbenzene, cumene, mesitylene, tert-butylbenzene, pseudocumene, trimethylhexane, octane, tetrachloroethane, nonane, chlorobenzene, ethylcyclohexane, m-dichlorobenzene, sec-butylbenzene, p-dichlorobenzene, decane, p-cymene, o-dichlorobenzene, butylbenzene, decahydronaphthalene, tetrahydronaphthalene, dodecane, naphthalene, cyclohexylbenzene, and the like, and the organic solvent may be used alone or as a mixture type of two or more thereof.

The amount used of the organic solvent is not specifically limited, but is appropriate in a range of about 1-20 times (based on weight), more preferably, about 2-10 times (based on weight) the amount used of a primary amine which is injected as a raw material considering that the reaction is smoothly performed and economic conditions are satisfied. If the amount used of the organic solvent is less than twice, the effective removal of water produced via the dehydration ring-closure reaction of N-substituted maleamic acid from a reaction system is not easy, and defects of decreasing yield arise. If the amount exceeds 10 times, an excessive amount of energy is consumed during the separating process of the organic solvent from a synthesized N-substituted maleimide solution, and it is undesirable from an economic standpoint.

In addition, the organic solvent is required to be determined considering environmental factors, the solubility of N-substituted maleimide, cost, and handling availability, and further, a solvent appropriate for removal and reuse after finishing the reaction is required to be selected. Here, the maleic anhydride and the primary amine may be dissolved in the same organic solvent or in different organic solvents, and preferably, dissolved in the same organic solvent.

In addition, if maleic anhydride or a primary amine is used in a solution type dissolved in an organic solvent, the concentration of the maleic anhydride or the primary amine may be any concentration by which the maleic anhydride or the primary amine could be dissolved, without specific limitation. Particularly, 0 to 500 g, more preferably, 10 to 200 g of an organic solvent based on 100 g of maleic anhydride is preferably added for dissolution. In addition, 0 to 500 g, more preferably, 5 to 200 g of an organic solvent based on 100 g of a primary amine is preferably added for dissolution.

In an embodiment of the present invention, the primary amine may use one type of primary amines selected from saturated or unsaturated alkylamine having 1-20 carbon atoms, cycloalkylamine having 5-20 carbon atoms cycloalkylamine having 6-20 carbon atoms, or aromatic alkylamine having 6-20 carbon atoms, and may particularly use one or more selected from the group consisting of methylamine, ethylamine, n-propylamine, isopropylamine, n-butylamine, sec-butylamine, iso-butylamine, tert-butylamine, n-hexylamine, n-octylamine, n-decylamine, n-dodecylamine, cyclohexylamine and aniline. To synthesize the N-phenyl maleimide of the present invention, aniline may be used as the primary amine.

In the present invention, the amount used of the maleic anhydride may preferably be from 1.0 to 1.3 molar ratio based on the primary amine used during synthesizing N-substituted maleimides. If less than 1.0 molar ratio of the maleic anhydride is used, defects of decreasing yield and increasing by-products arise, and if 1.3 molar ratio or more thereof is used, an excessive amount of unreacted maleic anhydride may remain after synthesizing N-substituted maleimide, which is economically undesirable.

Meanwhile, most of the catalysts used in the conventional synthesis method of N-substituted maleimide directly uses a catalyst in a liquid phase with a homogeneous system or uses a carrying catalyst in which an active component with a homogeneous system is carried in a carrier. However, if the liquid phase catalyst with a homogeneous system is used, the loss of the catalyst may arise during the separating process of a product from the catalyst via layer separation using a polarity difference after finishing the synthesis reaction. If the carrying catalyst is used, the loss of active components may arise due to water which is a by-product produced during the synthesis process of N-substituted maleimide, and the active component is required to be supplemented. The supplement of the active component is also possible after separating and drying the carrying catalyst, and thus, the process is complicated and the supplement of the active component is not an easy task.

Different from the conventional synthesis method, in the synthesis method of N-substituted maleimide of the present invention, N-substituted maleimides are synthesized using not a liquid phase catalyst with a homogeneous system or a carrying catalyst but a solid acid catalyst with a non-homogeneous system, and the present invention is characterized in solving the conventionally issued defects. Meanwhile, in the present invention, the homogeneous system means that the phases of the reactants for the synthesis reaction of N-substituted maleimides and the catalyst are the same, and the non-homogeneous system means that the phases of the reactants and the catalyst are different.

More particularly, the solid acid catalyst with a non-homogeneous system, used in the present invention is characterized in a zirconium(IV) hydrogen phosphate.

The zirconium(IV) hydrogen phosphate, $Zr(HPO_4)_2$, is an acidic and inorganic cation exchange material which has a lamellar structure and has high thermal and chemical stability, solid ion conductivity, resistance to ionization radiation, and introducing properties of molecules having different sizes and different types in the layers thereof. The zirconium hydrogen phosphate may be present in various states having various interlamellar spaces and crystal structures, and the most widely known zirconium hydrogen phosphate is an alpha type of $Zr(HPO_4)_2 \cdot H_2O$ and a gamma type of $Zr(PO_4)(H_2PO_4) \cdot 2H_2O$. The zirconium hydrogen phosphate may be utilized in various fields including drug delivery, catalyst action, a nano composite, nuclear waste management, a clinic catapult, and the like.

In the present invention, the zirconium hydrogen phosphate used as the solid acid catalyst is not the crystalline structure of alpha type or gamma type but a non-crystalline zirconium hydrogen phosphate, and the hydration degree thereof may change according to reaction conditions. The zirconium hydrogen phosphate may be represented by the following Formula 1:

  [Formula 1]

(in Formula 1, 0.5≤x≤1.5, 0≤a≤8, 0≤b≤8, and 1≤c≤4.)

As described above, the synthesis method of N-substituted maleimides of the present invention may minimize the possibility of catalyst loss by using a solid acid catalyst having a non-homogeneous system which has a different state from the reactants of the synthesis reaction of N-substituted maleimides, and is characterized in achieving high synthesis yield of N-substituted maleimides by using the zirconium hydrogen phosphate among the solid acid catalysts.

Particularly, the catalyst of the present invention is a solid having a different state from the reactants, and there is no concern to arise the loss of active components due to water which is a by-product produced during synthesizing N-substituted maleimide and the catalyst loss during a layer separation process after finishing the synthesis reaction. In addition, the zirconium hydrogen phosphate used in the present invention is structurally very stable, and has low reactivity with water. Accordingly, the supplement and regeneration of a catalyst during the reaction is not essentially required, and the effect of simplifying the synthesis process of N-substituted maleimides is also attained.

In addition, the zirconium hydrogen phosphate of the present invention serves higher synthesis yield of N-substituted maleimides than other solid acid catalysts. Particularly, if the zirconium hydrogen phosphate is added in a weight ratio of 0.06 or more based on the reaction solvent injected, the synthesis yield of N-substituted maleimides may become 70% or more.

Meanwhile, the solid acid catalyst of a non-homogeneous system of the present invention is required to be injected in an appropriate amount considering process operation and costs, and particularly, injected in a weight ratio of 0.01 to 1.0, more particularly, a weight ratio of 0.05 to 0.5 based on the reaction solvent injected is preferable.

If the injection amount is less than 0.01 weight ratio, the conversion ratio to N-substituted maleamic acid per unit hour is low, and total reaction time is required to increase, and if the amount is greater than 1.0 weight ratio, the intermediate reaction solid content may increase according to the production of N-substituted maleamic acid which is an intermediate product and stirring may not be smooth.

In addition, according to circumstances, the reaction may be performed in coexistence with a metal-containing compound or a stabilizer in a reaction system. In this case, the metal-containing compound used is not specifically limited, but may include at least one oxide of a metal selected from the group consisting of zinc, chromium, palladium, cobalt, nickel, iron and aluminum, acetates, maleates, salts of succinic acid, nitrates, phosphates, chlorides and sulfates. Among them, particularly effective one is zinc acetate. The amount used thereof is 0.005 to 0.5 mol %, preferably, 0.01 to 0.1 mol % as a metal, based on maleic anhydride and/or a primary amine, as raw materials.

In addition, as the stabilizer, methoxybenzoquinone, p-methoxyphenol, phenothiazine, hydroquinone, alkylated diphenylamines, methylene blue, tert-butyl catechol, tert-butylhydroquinone, zinc dimethyldithio carbamate, copper dimethyldithiocarbamate, copper dibutyldithiocarbamate, copper salicylate, thiodipropionic acid esters, mercaptobenzimidazole, triphenyl phosphite, alkylphenols, alkylbisphenols, etc. are used. The effect of the stabilizer is the role of stable presence without modification of N-substituted maleimides produced by dehydration ring-closure imidization reaction under the high temperature of corresponding imidization reaction. The amount added of the stabilizer is not specifically limited, but may be used in 0.001 to 0.5 mol % with respect to maleic anhydride and/or a primary amine, which are raw materials. Here, with such addition amount, the stabilization effect may be sufficiently shown, and defects of being mixed and included in a product may be avoided.

In the synthesis method of N-substituted maleimides of the present invention, the reaction temperature of the synthesis reaction of N-substituted maleimides of step 1) may be generally from 50 to 200° C., and more particularly, 100 to 140° C. is preferable. If the temperature of the synthesis reaction is less than 50° C., defects of decreasing yield arise, and if the temperature is 200° C. or higher, the polymerization of the N-substituted maleimides thus synthesized is inhibited due to side-reactions, and defects of decreasing the purity and yield of the N-substituted maleimides thus synthesized arise.

In the present invention, the reaction pressure is not specifically limited, and may be extensively selected from reduced pressure, atmospheric pressure and pressurized state. The reaction time may be changed according to conditions such as the type of solvents, the injection amount of raw materials, the amount of a catalyst, and the reaction temperature, and may be generally from 1 to 16 hours, more preferably, from 1 to 10 hours.

Under such reaction conditions, the dehydration ring-closure imidization reaction of N-substituted maleamic acid may be efficiently performed, and N-substituted maleimide may be efficiently obtained.

Step 2)

Step 2) according to an embodiment of the present invention is a step for separating and recovering a catalyst for recycle, and is characterized in separating and recovering the catalyst from a solution including N-substituted maleimides.

In the conventional synthesis method using a catalyst of a homogeneous system or a carrying catalyst, a catalyst was separated and recovered via processes of firstly separating a solution layer in which N-substituted maleimides were dissolved from a catalyst layer to perform layer separation, secondly removing catalyst remaining in a product and removing impurities via washing with solvents. However, in this case, defects were generated including the separation of the catalyst of a homogeneous system was not easy, the loss of active components from a carrier in the carrying catalyst arose, and a large amount of waste water was produced and the separating and recovering processes were difficult and complicated.

In addition, delamination was not easy at a high temperature such as the reaction temperature of the synthesis reaction of N-substituted maleimides, and a cooling process for delamination was required, and a re-heating process for the re-use of the catalyst was performed. And defects of requiring additional energy injection according to the cooling and re-heating arose.

However, the catalyst used in the synthesis method of N-substituted maleimides of the present invention is a solid acid catalyst, and uses a zirconium hydrogen phosphate which is a structurally or chemically stable solid acid. Thus, cooling and re-heating processes are not necessary, additional injection of energy is not necessary, and the separation and recovery of the catalyst may be possible by simple filtering in a temperature range from the lowest temperature at which the product is not precipitated as a solid in a solution phase including a product to the boiling point of a solution including a product, more preferably, at the high temperature of 70 to 160° C., thereby simplifying the separation and recovery processes of the catalyst.

Meanwhile, if the separated and recovered catalyst is re-used in a next period reaction, the activity of the catalyst is degraded due to the loss of active components or the damage of the active components due to impurities, and the reaction yield is also decreased proportionally in general.

The types of washing solvents used for washing impurities in a washing or firing process for regenerating the activity of the catalyst were limited in the conventional synthesis method, and the regeneration of the catalyst via a simple firing process was impossible and the catalyst was required to be replaced.

However, in the present invention, a solid acid catalyst having a non-homogeneous system is used as a catalyst, and if the activity of the separated and recovered catalyst is partly decreased, the regeneration of the catalyst while maintaining the stability of the catalyst is possible via the washing using a washing solvent without limiting the type of the catalysts. If the activity is completely decreased, and the catalyst becomes completely inactive, the catalyst may be easily regenerated via a firing process.

The washing solvent used in the washing process may be polar solvents, without limitation, and particularly, at least one polar solvent selected from the group consisting of water, acetone, sulfoxides and cyclic polar organic solvents containing oxygen may be used.

The synthesis method of N-substituted maleimides of the present invention may reuse such separated, recovered and regenerated catalyst after mixing with an organic solvent of the same type as one used for the synthesis reaction of N-substituted maleimides for securing liquidity, and transfer thereof to a reactant storage tank or a synthesis reactor.

Meanwhile, concerning the reuse of the washing solvent, in the conventional carrying catalyst carrying a phosphoric acid component (active component), the phosphoric acid component was dissolved in the washing solvent together with impurities, and the reuse thereof was impossible, because when the washing solvent was injected to a distillation process for recycle, it was apprehended that a distillation process equipment might be corroded by the phosphoric acid component at a high temperature. However, the synthesis method of N-substituted maleimides of the present invention utilizes a solid acid catalyst as the catalyst, and the washing solvent of the present invention also has subsidiary advantages of being transferred to a distillation process and reused.

As described above, the synthesis method of N-substituted maleimides of the present invention uses a zirconium (IV) hydrogen phosphate solid acid catalyst, which is a non-homogeneous system, as a catalyst, and the catalyst loss may be minimized, and defects of complicated separation, recovery, and regeneration processes of a catalyst which were issued in the conventional synthesis method including the limitation of solvents used for separating the catalyst, the generation of a large amount of waste water in the removing process of remaining catalyst and impurities, and the necessity of energy injection according to the conductance of cooling and re-heating, may be solved.

Example 1

To a 100 ml reactor provided with a stirrer, a thermometer, a water separator and a cooler, 20 ml of o-xylene as a solvent, 2.5 g of aniline, 2.9 g of maleic anhydride molten at 80° C., and 1.249 g of zirconium(IV) hydrogen phosphate solid acid catalyst were added, and the temperature of a reaction system was elevated to 125° C. to synthesize N-phenyl maleimide. During the reaction, water produced via dehydration ring-closure reaction was removed out of the reaction system together with o-xylene via azeotropic distillation. The synthesis reaction was additionally performed for 4 hours while re-injecting the o-xylene removed from the reaction system into the reaction system. After finishing the synthesis reaction, a carrying carrier was separated via filtering, and an N-phenyl maleimide o-xylene solution was recovered. The temperature of the recovered N-phenyl maleimide o-xylene solution was elevated to 80° C. under a reduced pressure of 10 mmHg, and o-xylene was removed via distillation under reduced pressure to synthesize N-phenyl maleimide.

Example 2

N-phenyl maleimide was synthesized by the same method as Example 1 except for adding 0.8 g of the zirconium(IV) hydrogen phosphate solid acid catalyst in Example 1.

Example 3

N-phenyl maleimide was synthesized by the same method as Example 1 except for adding 0.6 g of the zirconium(IV) hydrogen phosphate solid acid catalyst in Example 1.

Comparative Examples 1 to 10

Each N-phenyl maleimide was synthesized by the same method as Example 1 except for using the solid acid catalyst written in Table 1 below instead of the zirconium(IV) hydrogen phosphate solid acid catalyst in Example 1.

Experimental Example

After finishing the synthesis reaction of each N-phenyl maleimide of Example 1 and Comparative Examples 1 to 10, a produced solution was collected, and a product was analyzed by liquid chromatography (LC). The yield of N-phenyl maleimide (PMI), ANL (aniline) standard selectivity, and the amounts of 2-anilino-N-phenyl succinimide (APSI) and others were measured and listed in Table 1 below.

*PMI yield=(aniline conversion ratio)×(PMI selectivity on products)

*ANL standard selectivity=(PMI mole number on products)/(converted ANL mole number)

TABLE 1

| Reaction conditions | | PMI yield (%) | ANL standard selectivity (mol %) | APSI (mol %) | Others (mol %) |
|---|---|---|---|---|---|
| Catalyst | Series | | | | |
| Example 1 | ZrP | Phosphate series | 77.2 | 77.2 | 2.9 | 19.9 |
| Example 2 | (zirconium phosphate) | | 38.9 | 38.9 | 0.7 | 58.63 |
| Example 3 | | | 15.8 | 15.8 | 0.36 | 83.85 |
| Comparative Example 1 | SnPO (tin phosphate) | | 7.40 | 7.42 | 0.67 | 91.92 |
| Comparative Example 2 | BPO$_4$ (boron phosphate) | | 0.04 | 0.04 | 0.00 | 99.96 |
| Comparative Example 3 | FePO$_4$ | | 0.02 | 0.02 | 0.28 | 99.70 |
| Comparative Example 4 | B-zeolite (cp811c-300) | Zeolite series | 3.23 | 3.23 | 0.25 | 96.52 |
| Comparative Example 5 | Y-zeolite (CBA300) | | 1.75 | 1.88 | 0.51 | 97.61 |
| Comparative Example 6 | Y-zeolite (CBA500) | | 1.52 | 1.55 | 1.42 | 97.04 |
| Comparative Example 7 | ZSM-5 | | 0.69 | 0.69 | 0.89 | 98.42 |
| Comparative Example 8 | CaSO$_4$ | Sulfate series | 0.07 | 0.07 | 0.20 | 99.73 |
| Comparative Example 9 | MnSO$_4$ | | 0.02 | 0.02 | 0.05 | 99.93 |
| Comparative Example 10 | Amberlite IR120H (acidic cation exchange resin) | Ion exchange resin series | 4.51 | 4.51 | 0.00 | 95.49 |

As shown in Table 1 above, when comparing Examples 1 to 3 of the present invention with Comparative Examples 1 to 10, it was found that Comparative Examples 1 to 10 had not high yield of N-phenyl maleimide (PMI) or ANL (aniline) standard selectivity even though using the same solid acid catalyst or a phosphate series catalyst among them as in Examples 1 to 3.

On the contrary, Examples 1 to 3 using the zirconium hydrogen phosphate solid acid catalyst were found to have quite excellent N-phenyl maleimide (PMI) yield and ANL (aniline) standard selectivity. Particularly, Example 1 in which the same amount as the catalyst addition amount of the comparative examples showed remarkably excellent synthesis efficiency when compared to that of the comparative examples. Even for Examples 2 and 3 in which about 50 to 60 wt % of the catalyst addition amount of the comparative examples, it was found that synthesis efficiency was still better than the comparative examples.

Therefore, if a zirconium(IV) hydrogen phosphate solid acid catalyst is used as the catalyst of the synthesis reaction of N-substituted maleimides, it could be found that catalyst loss may be minimized, the separating and recovering processes of the catalyst may be simplified, and if the activity of the separated and recovered catalyst is decreased, the complete regeneration of the catalyst may be possible via washing or firing, and process may be simple without limitation on the selection of washing solvents, and further, synthesis yield may be also excellent.

The above-described explanation of the present invention is for illustration, and it will be understood that a person skilled in the art would easily modify into other particular forms without changing the technical spirit or essential features of the present invention. Therefore, the above-described embodiments should be understood illustrative in all aspects but are not limited.

The invention claimed is:

1. A method of synthesizing N-substituted maleimides, the method comprising:
   1) a step of injecting maleic anhydride and a primary amine in the presence of an organic solvent and a catalyst to synthesize N-substituted maleimides; and
   2) a step of separating the catalyst from a solution comprising the N-substituted maleimides,
   wherein the catalyst is a zirconium(IV) hydrogen phosphate solid acid catalyst.

2. The method of synthesizing N-substituted maleimides of claim 1, wherein the zirconium hydrogen phosphate is non-crystalline.

3. The method of synthesizing N-substituted maleimides of claim 1, wherein the zirconium hydrogen phosphate is represented by the following Formula 1:

$Zr_x(H_aPO_b)_c$     [Formula 1]

in which $0.5 \leq x \leq 1.5$, $0 \leq a \leq 8$, $0 \leq b \leq 8$, and $1 \leq c \leq 4$.

4. The method of synthesizing N-substituted maleimides of claim 1, wherein the catalyst is added in a weight ratio of 0.01 to 1.0 with respect to a reaction solvent injected.

5. The method of synthesizing N-substituted maleimides of claim 1, wherein separating the catalyst comprises filtering the solution at a temperature of 70° C. to 160° C.

6. The method of synthesizing N-substituted maleimides of claim 1, further comprising a step of regenerating the catalyst via washing or firing the separated catalyst.

7. The method of synthesizing N-substituted maleimides of claim 6, wherein the washing of the catalyst uses one or more polar solvents selected from a group consisting of water, acetone, sulfoxides, and cyclic polar organic solvents containing oxygen.

8. The method of synthesizing N-substituted maleimides of claim 6, wherein the regenerated catalyst is reused.

9. The method of synthesizing N-substituted maleimides of claim 1, wherein the organic solvent is one or more selected from the group consisting of benzene, toluene, xylene, o-xylene, ethylbenzene, isopropylbenzene, cumene, mesitylene, tert-butylbenzene, pseudocumene, trimethylhexane, octane, tetrachloroethane, nonane, chlorobenzene, ethylcyclohexane, m-dichlorobenzene, sec-butylbenzene, p-dichlorobenzene, decane, p-cymene, o-dichlorobenzene, butylbenzene, decahydronaphthalene, tetrahydronaphthalene, dodecane, naphthalene, and cyclohexylbenzene.

10. The method of synthesizing N-substituted maleimides of claim 1, wherein the primary amine is one or more selected from the group consisting of methylamine, ethylamine, n-propylamine, isopropylamine, n-butylamine, sec-butylamine, iso-butylamine, tert-butylamine, n-hexylamine, n-octylamine, n-decylamine, n-dodecylamine, cyclohexylamine, and aniline.

11. The method of synthesizing N-substituted maleimides of claim 1, wherein the N-substituted maleimide is one or more selected from the group consisting of an N-alkyl maleimide; N-benzylmaleimide; N-cycloalkyl maleimide; N-phenyl maleimide; and N-substituted phenyl maleimide in which a phenyl group is substituted with a nitro, alkoxy, alkyl, carboxyl, hydroxyl, or a halogen atom.

* * * * *